United States Patent
Lenev et al.

(10) Patent No.: US 11,291,982 B2
(45) Date of Patent: Apr. 5, 2022

(54) CATALYST SYSTEM USED IN OLEFIN OLIGOMERIZATION AND METHOD FOR OLEFIN OLIGOMERIZATION

(71) Applicant: PUBLIC JOINT STOCK COMPANY "SIBUR HOLDING", Tobolsk (RU)

(72) Inventors: Denis Alekseevich Lenev, Khimki (RU); Rafael Acevedo Forero, Tomsk (RU)

(73) Assignee: PUBLIC JOINT STOCK COMPANY SIBUR HOLDING, Tobolsk (RU)

(*) Notice: Subject to any disclaimer, the term of this patent is extended or adjusted under 35 U.S.C. 154(b) by 259 days.

(21) Appl. No.: 16/349,922

(22) PCT Filed: Nov. 14, 2016

(86) PCT No.: PCT/RU2016/000778
§ 371 (c)(1),
(2) Date: May 14, 2019

(87) PCT Pub. No.: WO2018/088924
PCT Pub. Date: May 17, 2018

(65) Prior Publication Data
US 2019/0336955 A1 Nov. 7, 2019

(51) Int. Cl.
*C07C 2/32* (2006.01)
*B01J 31/22* (2006.01)
*B01J 31/12* (2006.01)
*B01J 31/18* (2006.01)
*B01J 37/34* (2006.01)

(52) U.S. Cl.
CPC ......... *B01J 31/2239* (2013.01); *B01J 31/122* (2013.01); *B01J 31/181* (2013.01); *B01J 37/346* (2013.01); *C07C 2/32* (2013.01); *B01J 2231/20* (2013.01); *B01J 2531/62* (2013.01); *C07C 2531/34* (2013.01)

(58) Field of Classification Search
None
See application file for complete search history.

(56) References Cited

U.S. PATENT DOCUMENTS

| | | |
|---|---|---|
| 6,455,648 B1 | 9/2002 | Freeman et al. |
| 8,084,659 B2 | 12/2011 | Gartside et al. |
| 8,252,955 B2 | 8/2012 | Gao et al. |
| 8,252,956 B2 | 8/2012 | Gao et al. |
| 2008/0177122 A1 | 7/2008 | Knudsen et al. |

FOREIGN PATENT DOCUMENTS

| | | |
|---|---|---|
| RU | 2104088 | 2/1998 |
| RU | 2254318 | 6/2005 |
| RU | 2412002 | 2/2011 |
| WO | 99/19280 | 4/1999 |
| WO | 2011/140629 | 11/2011 |
| WO | 2012/092415 | 7/2012 |
| WO | 2015/133805 | 9/2015 |
| WO | 2016/105228 | 6/2016 |
| WO | WO 2016/105227 A1 * | 6/2016 |

OTHER PUBLICATIONS

International Search Report and Written Opinion dated Aug. 24, 2017, directed to PCT/RU2016/000778; 5 pages.
Nexant Inc. (Apr. 2008). "Report Abstract: Alpha Olefins PERP06/07-5" CHEMSYSTEMS PERP Program: 13 pages.

* cited by examiner

*Primary Examiner* — Yun Qian
(74) *Attorney, Agent, or Firm* — Morrison & Foerster LLP (57) ABSTRACT

The invention relates to the field of oligomerization of olefins to produce linear α-olefins, in particular hexene-1, with the use of a catalyst system. The catalyst system comprises a chromium source compound, a nitrogen-containing ligand, alkylaluminum, and a zinc compound, wherein catalyst system is activated during its preparation by 1) heating some and SHF irradiation (microwave irradiation) of alkylaluminum or a mixture of the alkylaluminum and the zinc compound, or by 2) heating alkylaluminum or a mixture of the alkylaluminum and the zinc compound, followed by holding (aging) the prepared catalyst system for a certain period of time.

28 Claims, 2 Drawing Sheets

CATALYST SYSTEM USED IN OLEFIN OLIGOMERIZATION AND METHOD FOR OLEFIN OLIGOMERIZATION

CROSS-REFERENCE TO RELATED APPLICATIONS

This application is a U.S. national phase patent application of International Patent Application No. PCT/RU2016/000778, filed Nov. 14, 2016, which is hereby incorporated by reference in the present disclosure in its entirety.

TECHNICAL FIELD OF THE INVENTION

The invention relates to the field of oligomerization of olefins to produce linear α-olefins, in particular hexene-1, used in the production of low-, medium-, and high-density linear polyethylene, poly-α-olefins for anti-turbulent additives, and the like.

BACKGROUND OF THE INVENTION

During oligomerization of olefins, internal olefin impurities with double bonds in positions other than the α-position, vinylidene impurities, which are branched α-olefins, and polymer by-products are formed along with a target linear terminal product. Thus, trimerization of ethylene gives not only the target product, which is hexene-1, but also by-products, such as trans-hexene-2, cis-hexene-2, trans-hexene-3, and cis-hexene-3, i.e. internal olefins, and vinylidene isomers, for example, 2-methylpentene-1.

Such by-products are unwanted impurities of the target linear terminal product. For example, the internal olefins formed through trimerization of ethylene do not co-polymerize with ethylene on traditional catalysts for the synthesis of linear low-density polyethylene (LLDPE) and high-density polyethylene (HDPE), and reduce the activity of the olefin polymerization catalysts.

In addition, in the case of production of LLDPEs and HDPEs, the rate of conversion of hexene-1 to co-polymers may be lower than 1, and hexene-1 needs, therefore, to be recycled. During the recycle, isomeric impurities in hexene-1 can accumulate and, therefore, a part of hexene-1 must be continuously removed from the system and replaced with a fresh portion of hexene-1. In order to reduce the loss of hexene-1 during the recycle, high requirements are imposed to the isomeric purity of hexene-1.

The prior art discloses a method for purification of α-olefins by rectification in specific columns for fine purification of α-olefins ("Super Six" column) (PERP Report Alpha Olefins 06/07-5, Nexant Inc., 2008). However, the isolation of isomerically pure α-olefin by rectification is a difficult process since internal isomers have a boiling point close to that of a target α-olefin, and their separation, therefore, requires large energy consumption and significant capital and operating expenditures.

Patents RU2254318 and U.S. Pat. No. 8,084,659 provide a method for increasing the isomeric purity of α-olefin by isomerization of internal olefins and vinylidene impurities in the presence of a heterogeneous catalyst, followed by rectification of a target α-olefin. In U.S. Pat. No. 5,144,053, which relates to the production of 1-olefin from internal olefins, internal hexenes are isomerized in the presence of a homogenous nickel catalyst, and an organoaluminum compound is used to isolate a target hexene-1 by displacing branched alkyls based on internal hexenes to form tri-n-hexylaluminum. A disadvantage of the method is the use of an additional step (isomerization of internal olefins) to increase the isomeric purity of the target α-olefin, labor-intensiveness of the process of separating the target α-olefin from residual isomers by rectification since internal isomers have a boiling point close to that of α-olefin, and a need for additional reagents for isolation of isomerically pure α-olefin.

Methods also are known for increasing the isomeric purity of α-olefins directly in the selective production of α-olefins by using ligands with a complex structure in an oligomerization catalyst system. U.S. Pat. No. 8,252,955 and U.S. Pat. No. 8,252,956 provide ethylene oligomerization catalyst systems allowing the production of target α-olefins with a high selectivity. A disadvantage of these catalyst systems is a need for expensive components, such as P—N—P ligands, methylalumoxane and/or modified methylalumoxane (MAO and MMAO, respectively).

The prior art also discloses a method for increasing selectivity to a target α-olefin by adding a zinc compound to a catalyst composition used for selective oligomerization of olefins. Thus, application WO2011140629 provides a method for oligomerization of ethylene to produce hexene-1 in the presence of a catalyst system containing a chromium source, a P—N—P ligand, methylalumoxane, and a zinc compound. However, the maximum isomeric purity of hexene-1 is only 96%. A disadvantage of the method is the use of expensive P—N—P ligands in the catalyst system and the formation of a relatively large amount of oligomers containing 10 and more carbon atoms.

U.S. Pat. No. 6,455,648 and applications WO9919280 and WO2015133805 disclose a method of trimerization of ethylene to hexene-1 in the presence of a catalyst system comprising a chromium source, a pyrrole ligand, and alkylaluminum as an activator, without additional operations for increasing the activity and selectivity of the catalyst system. The maximum isomeric purity of hexene-1 is 99.2-99.6%. The main disadvantage of this method is that the oligomerization process is carried out at increased pressure of ethylene (about 50 atm and more), which requires special equipment and leads to a large capital expenditures.

The method for oligomerization of ethylene, disclosed in patent RU2412002 and application WO2012092415, is closest to the claimed method. In the invention according to patent RU2412002, the oligomerization process is carried out in the presence of a catalyst system comprising a chromium source, a pyrrole ligand, and alkylaluminum. The activity and selectivity of the catalyst system is increased by exposing alkylaluminum comprised in the oligomerization catalyst system to SHF irradiation, and by the use of a halogen-containing compound as an additional component of the catalyst system. However, the maximum isomeric purity of hexene-1 is only 97.4%. A disadvantage of the method is that the oligomerization process is carried out at a relatively low temperature, in particular at of 50 to 60° C., at which a polymer by-product is not dissolved, which leads to the formation of deposits in the reactor, heat exchangers, and other equipment.

The application WO2012092415 provides a method for increasing the activity and selectivity of an olefin oligomerization catalyst system comprising a chromium source, a P—N—P ligand, and alkylaluminum, by holding (aging) the catalyst system for at least 20 min. However, the maximum isomeric purity of hexene-1 is only 95%. A disadvantage of the method is a need for an expensive and hardly accessible P—N—P ligand used in the catalyst system.

Thus, the prior art methods for increasing selectivity to α-olefin are insufficiently effective, expensive, and energy consuming.

In this connection, one of perspective directions is the development of an effective method for oligomerization of olefins, characterized by a high selectivity to a target α-olefin.

SUMMARY OF THE INVENTION

The object of the present invention is to develop a method for oligomerization of olefins, characterized by an increased selectivity to a target linear α-olefin compared to all its isomers.

This object is addressed by the provision of a catalyst system used in oligomerization of olefins, comprising a chromium source, a nitrogen-containing ligand, alkylaluminum as an activator, and a zinc compound. In addition, a characteristic feature is that the used catalyst system is activated during its preparation by 1) heating some of components of the catalyst and SHF irradiation (microwave irradiation) or by 2) heating separate components, followed by holding (aging) the prepared catalyst system for a certain period of time. In addition, alkylaluminum and optionally the zinc compound are subjected to heating and SHF irradiation (microwave irradiation), if necessary, to prior to the mixing thereof with the other components of the catalyst system.

Thus, the present invention relates to a method for preparing a catalyst system (variants), a catalyst system prepared by this method, a method for oligomerization of olefins in the presence of a catalyst system prepared by the method according to the present invention, and to α-olefins prepared by this method.

According to one embodiment of the invention, a method for preparing a catalyst system used in oligomerization of olefins comprises mixing a chromium source compound, a nitrogen-containing ligand, alkylaluminum, and a zinc compound, wherein the alkylaluminum or a mixture of the alkylaluminum and the zinc compound is activated by heating and SHF irradiation (microwave irradiation) prior to the mixing thereof with the other components of the catalyst system.

According to another embodiment of the invention, a method for preparing a catalyst system used in oligomerization of olefins and comprising a chromium source compound, a nitrogen-containing ligand, alkylaluminum, and a zinc compound comprises activating the alkylaluminum or a mixture of the alkylaluminum and the zinc compound by heating prior to the mixing thereof with the other components of the catalyst system, mixing the activated alkylaluminum or mixture of the alkylaluminum and the zinc compound with the other components of the catalyst system to prepare said catalyst system, and holding (aging) the prepared catalyst system for a certain period of time.

Although a prior art application (for example, US20080177122) discloses that an increased temperature in synthesis of a selective chromium-pyrrole catalyst system or addition of the system to an oligomerization reaction at a temperature of higher than 25° C. negatively affects its activity and selectivity, the inventors have found that the use of the catalyst system in oligomerization of olefins, wherein the catalyst system was prepared by heating alkylaluminum and optionally a zinc compound, followed by SHF irradiation (microwave irradiation) or holding (aging) the catalyst system for a certain period of time, provides an increase in the isomeric purity of the prepared α-olefin up to 99.9%.

The present invention provides an increased selectivity of the olefin oligomerization catalyst system to the yield of a target linear α-olefin compared to the yield of all its isomers, which, in turn, allows reducing the loss of the linear α-olefin during recycling thereof in the production of polyolefins. The isomeric purity of α-olefin, in particular hexene-1, reaches 99.9%.

BRIEF DESCRIPTION OF THE DRAWINGS

FIGS. 1 and 2 are intended to illustrate the technical solutions disclosing the essence of the invention.

DETAILED DESCRIPTION OF THE INVENTION

Various aspects and embodiments of the invention are described in detail below.

According to one embodiment of the invention, a method is provided for oligomerization of olefins using a catalyst system that is prepared by mixing a chromium source compound, a nitrogen-containing ligand, alkylaluminum, and a zinc compound, wherein the alkylaluminum or a mixture of the alkylaluminum and the zinc compound is activated by heating and SHF irradiation (microwave irradiation) prior to the mixing thereof with the other components of the catalyst system.

Further, unless otherwise noted, irradiation used herein is SHF irradiation or microwave irradiation (which means the same).

Figure 1:
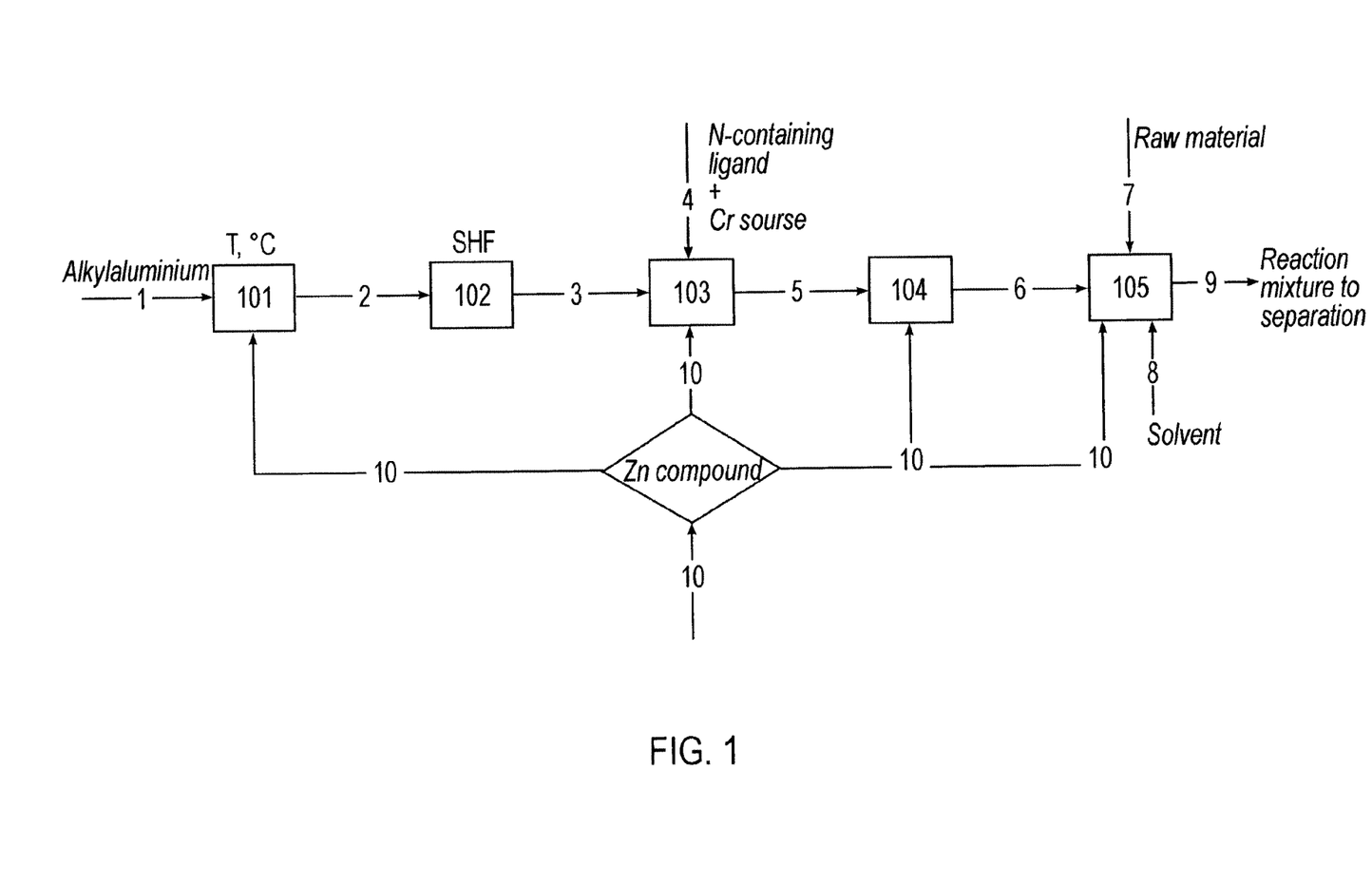
FIG. 1 is a flow chart demonstrating the sequence of the operations of the method according to the first embodiment of the present invention.

The technical essence of the method according to the first embodiment of the invention is shown in FIG. 1, wherein 101 is a heat-exchange unit for heating the supplied components of the catalyst system, 102 is a vessel in which the components of the catalyst system are subjected to SHF irradiation, 103 is a reactor in which all components of the catalyst system are mixed, 104 is an intermediate vessel for storage of the prepared catalyst system, and 105 is an oligomerization reactor.

According to this method, some of the components of the catalyst system, which are alkylaluminum (1) or a mixture of the alkylaluminum and a zinc compound (1 and 10), are supplied to the heat-exchange unit (101) to heat them, and then they are delivered to the vessel (102) where said components are subjected to SHF irradiation. Further, the activated components of the catalyst system (3) enter the reactor (103) where they are mixed with the other components including a chromium source and a nitrogen-containing ligand (4). The prepared catalyst system (5) is placed to the storage vessel (104) from which a required amount of the catalyst system is delivered to the oligomerization reactor (105) to which a solvent (8) and raw material (7) are also fed.

It should be noted that the zinc compound (line 10) can be added at any step of the method, including at the step of activating the components of the catalyst system in the unit (101), at the step of mixing the components of the catalyst system in the reactor (103) or during storage of the catalyst system in the vessel (104), as well as at the step of oligomerization in the reactor (105).

Alkylaluminum is activated by heating and SHF irradiation. Alkylaluminum may also be activated by heating and SHF irradiation together with the zinc compound. The heating of these components of the catalyst system is carried out up to at least 40° C., preferably to 50° C., most preferably to 60° C., wherein said components of the catalyst system are pre-heated or heated during SHF irradiation (microwave irradiation), prior to the mixing thereof with the chromium source and the nitrogen-containing ligand.

Alkylaluminum and the zinc compound may be subjected to heating and SHF irradiation in the form of compounds, preferably in a liquid state, and solutions in a hydrocarbon solvent, for example, in hexane, cyclohexane, $C_{10}$-$C_{12}$ hydrocarbons.

During the irradiation, it is necessary that the components of the catalyst system to be activated were in a vessel transparent for SHF-radiation, for example, in a vessel made of glass, fluorine plastic, and polypropylene.

The frequency of the used SHF-radiation may range from 0.2 to 20 GHz. The SHF-radiation with a frequency of 2.45 GHz is especially preferred because it does not generate RF interference and is broadly used in domestic and industrial SHF-radiation sources.

The rated power of the SHF-radiation is from 1 W to 5000 W per 1 g of the used alkylaluminum based on elemental aluminum.

For the best results, it is preferable that the time of irradiation be from 20 sec to 20 min, about 1 min, about 2 min, about 3 min, about 4 min, about 5 min, about 6 min, about 8 min, about 10 min, about 12 min, and preferably about 15 min. The irradiation for more than 20 min usually does not provide additional improvements to the properties of the catalyst system. The irradiation for less than 20 sec may be insufficient to provide a significant change in the properties of the components to be activated, which, in turn, results in the catalyst system with insufficiently increased activity and/or selectivity.

The alkylaluminum or mixture of the alkylaluminum and the zinc compound, which are activated by heating or SHF irradiation (microwave irradiation), is mixed with the chromium source and the nitrogen-containing ligand not more than 3 min after the irradiation, preferably not more than 1 min after the irradiation.

If the interval of time between the mixing of the irradiated alkylaluminum or mixture of the alkylaluminum and the zinc source with the chromium source and the nitrogen-containing ligand is 3 min or more, the properties of the prepared catalyst system are significantly deteriorated compared to those of the catalyst system for which said interval of time is less than 1 min.

The components of the catalyst system may be mixed by any method known in the art. The components of the catalyst system are mixed for from 1 to 30 min, preferably not less than 2 min, not less than 4 min, not less than 8 min, not less than 15 min, and not less than 25 min. Alternatively, the components to be activated by heating and subsequent SHF irradiation may be gradually supplied for mixing with the other components of the catalyst system directly from the vessel where they were SHF irradiated; therefore, the time of mixing may be any convenient time, without losing special properties of the irradiated component or mixture of components, which properties were acquired upon heating and SHF irradiation.

The order of mixing the components of the catalyst system is not important. It is preferable to add alkylaluminum and the zinc source to a mixture of the chromium source and the nitrogen-containing ligand. The components are mixed in any suitable device known in the art, for example, in a bubble unit, a stirred vessel, or a static mixer, in the presence of a hydrocarbon solvent.

According to another embodiment of the invention, where SHF irradiation is not required, the method for oligomerization of olefins is carried out using a catalyst system comprising a chromium source compound, a nitrogen-containing ligand, alkylaluminum, and a zinc compound, wherein the catalyst system is prepared by activating the alkylaluminum or a mixture of the alkylaluminum and the zinc compound by heating prior to the mixing thereof with the other components of the catalyst system, mixing the activated alkylaluminum or mixture of the alkylaluminum and the zinc compound with the other components of the catalyst system to prepare said catalyst system, and holding (aging) the prepared catalyst system for a certain period of time.

Figure 2:
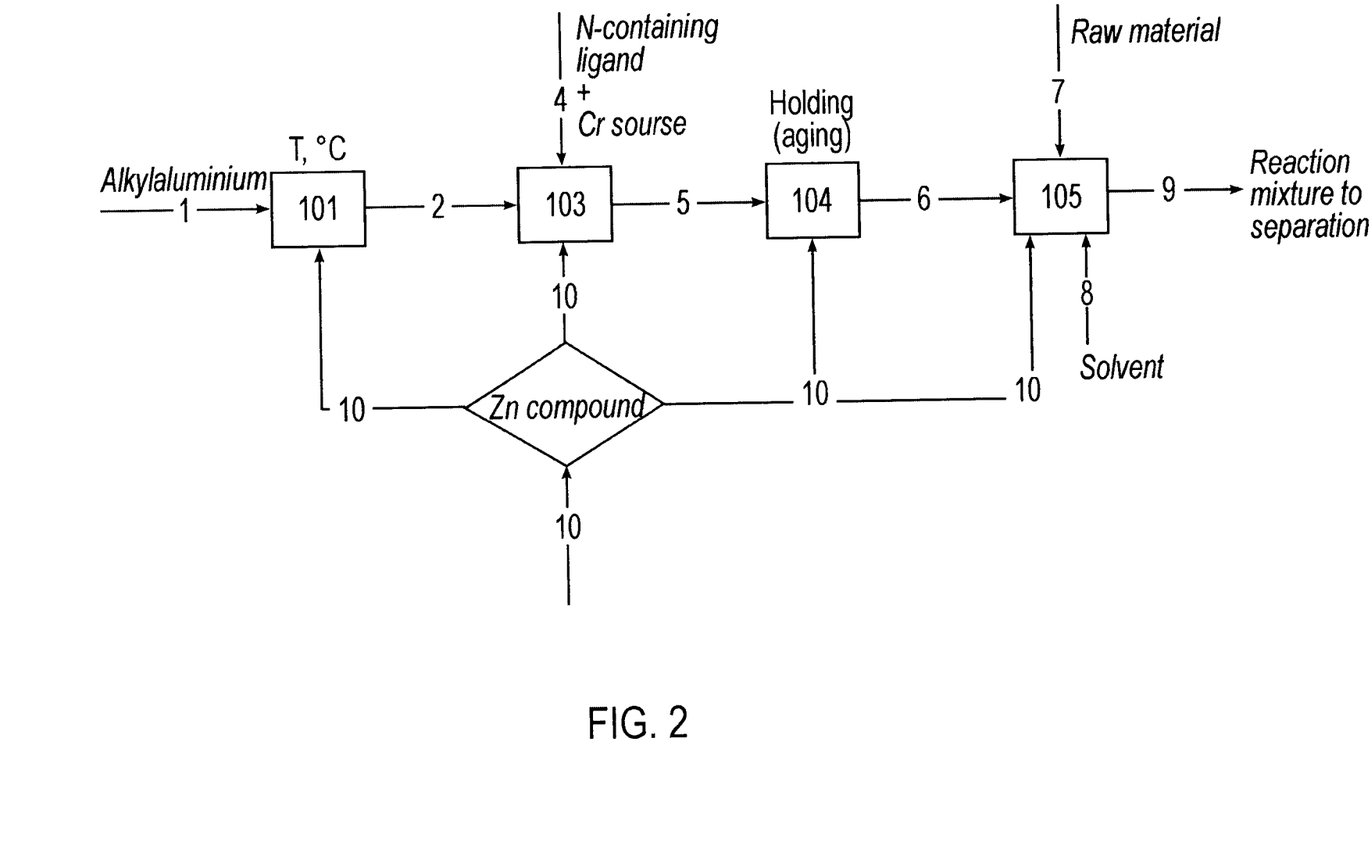
FIG. 2 is a flow chart demonstrating the sequence of the operations of the method according to the second embodiment of the present invention.

This variant is illustrated in FIG. 2, wherein 101 is a heat-exchange unit for heating the supplied components of the catalyst system, 103 is a reactor in which all components of the catalyst system are mixed, 104 is an intermediate vessel for storage of the prepared catalyst system, and 105 is an oligomerization reactor.

According to this method, some of the components of the catalyst system, which are alkylaluminum (1) or a mixture of the alkylaluminum and the zinc compound (1 and 10), are supplied to the heat-exchange unit (101) where they are heated, and then they are delivered to the reactor (103) where said components are mixed with the other components including the chromium source and the nitrogen-containing ligand (4). The prepared catalyst system (5) is hold (aged) in the storage vessel (104) for a certain period of time, and then a required amount of the system is delivered from said vessel to the oligomerization reactor (105) to which a solvent (8) and raw material (7) are also fed.

It should be noted that the zinc compound (line 10) may be added at any step of the method, including at the step of heating the components of the catalyst system in the unit (101), at the step of mixing the components of the catalyst system in the reactor (103), or during holding (aging) the catalyst system in the vessel (104), as well as at the step of oligomerization in the reactor (105).

The heating applies to alkylaluminum. Alkylaluminum can also be heated together with the zinc compound. These components of the catalyst are heated to at least 40° C., preferably to 50° C., most preferably to 60° C. The heating of these components is carried out prior to the mixing thereof with the other components of the catalyst system, in particular, prior to the mixing thereof with the chromium source and the nitrogen-containing ligand.

After the step of heating, the components of the catalyst system are mixed by any method known in the art for 1 to 30 min, preferably not less than 2 min, not less than 4 min, not less than 8 min, not less than 15 min, and not less than 25 min. The order of mixing the components of the catalyst system is not important. It is preferable to add the alkylaluminum and the zinc compound to a mixture of the chromium source and the nitrogen-containing ligand. The components are mixed in any suitable device known in the art in the presence of a hydrocarbon solvent.

The prepared catalyst system is hold (aged) for a certain period of time. The holding (aging) of the catalyst system may be carried out both with and without stirring and lasts for from 1 to 120 days, preferably for from 2 to days, most preferably for from 14 to 45 days. The catalyst system may be hold (aged) in any suitable device known in the art, for example in a stirred reactor, a mixer, a stirred vessel.

The holding (aging) of the catalyst system occurs at a temperature of from 10° C. to 130° C., preferably from 15° C. to 60° C., more preferably from 20° C. to 40° C. in an inert atmosphere at a pressure of from 0.5 to 10 atm, preferably from 1 to 5 atm, more preferably from 1 to 2 atm.

In the disclosed embodiments of the invention, both the first and the second ones, all steps of preparing the catalyst system are preferably carried out under conditions which exclude any contact of the components of the catalyst system with water and air oxygen.

In addition, the step of mixing the components of the catalyst system is carried out in the presence of a hydrocarbon solvent. Suitable hydrocarbon solvents include, but not are limited to, hexene-1, benzene, toluene, ethylbenzene, xylene, or a mixture thereof. Preferred solvents include aromatic hydrocarbons which provide an increased stability of the catalyst system and allow the production of a highly active and selective catalyst system. The aromatic hydrocarbon solvent is preferably selected from the group consisting of toluene, ethylbenzene, or a mixture thereof. Ethylbenzene is the most preferred aromatic hydrocarbon.

After the step of mixing and preparing the catalyst system, the hydrocarbon solvent may be removed from the mixture. As known from the prior art (patent RU2104088), the presence of unsaturated aromatic hydrocarbon in the reaction mixture during the oligomerization process may reduce the activity of the catalyst system and increase the amount of by-products, such as polymers. The solvent may be removed by any known method, for example, by degassing (vacuum treatment). However, it should be noted that when oligomerization of olefins is carried out at an increased temperature, the presence of an unsaturated hydrocarbon solvent, for example, such as ethylbenzene, may be preferred since said solvent increases the stability of the catalyst system.

The method of oligomerization of olefins comprises oligomerization of α-olefin-containing raw material under oligomerization conditions in the presence of a catalyst system that comprises a chromium source, a nitrogen-containing ligand, alkylaluminum, and a zinc compound and that is prepared according to one of the above-disclosed embodiments.

According to the present invention, the chromium source compound comprised in the catalyst system may be an organic and/or non-organic chromium compound. The oxidation degree of chromium in compounds may vary and be equal to 0, +1, +2, +3, +4, +5, and +6. Generally, the chromium source is a compound of the general formula $CrX_n$, wherein elements X may be the same or different organic and/or non-organic substituents, and n is an integer from 1 to 6. Organic substituents X may contain from 1 to 20 carbon atoms and may be alkyl, alkoxy, carboxy, acetylacetonate, amino, amido, or the like. Suitable inorganic substituents X include halides, sulfates, chromium oxides, and the like. Examples of the chromium source include chromium (III) chloride, chromium (III) acetate, chromium (III) 2-ethylhexanoate, chromium (III) acetylacetonate, chromium (III) pyrrolide, chromium (II) acetate, chromium (IV) dioxide dichloride ($CrO_2Cl_2$), and the like.

The nitrogen-containing ligand comprised in the catalyst system is an organic compound that comprises a pyrrole ring moiety, i.e. a 5-membered aromatic ring containing a nitrogen atom. Suitable nitrogen-containing ligands include, but are not limited to, pyrrole, 2,5-dimethylpyrrole, lithium pyrrolide ($C_4H_4NLi$), 2-ethylpyrrole, 2-allylpyrrole, indole, 2-methylindole, and 4,5,6,7-tetrahydroindole. Pyrrole or 2,5-dimethylpyrrole is more preferred.

The alkylaluminum comprised in the catalyst system may be an alkylaluminum compound and a halogenated alkylaluminum compound, an alkoxyaluminum compound, or a mixture thereof. To increase selectivity, it is preferable to use the mentioned above compounds, which were not in contact with water (non-hydrolized), of general formulas $AlR_3$, $AlR_2X$, $AlRX_2$, $AlR_2OR$, $AlRXOR$, and/or $Al_2R_3X_3$, wherein R is alkyl, and X is a halogen atom. Suitable alkylaluminum compounds include, but are not limited to, triethylaluminum, diethylaluminum chloride, tripropylaluminum, triisobutylaluminum, diethylaluminum ethoxide, ethylaluminum sesquichloride, or a mixture thereof. Triethylaluminum or a mixture of triethylaluminum and diethylaluminum chloride is preferred.

The olefin-oligomerization catalyst system comprises one or more zinc compounds. The zinc compound can be used as an individual compound and as a mixture with other compounds, for example, in the form of a solution in hydrocarbons.

Zinc compounds may be added directly to the catalyst system during its preparation, or separately, to an oligomerization reactor. The zinc compound may be used as an additional activator of the catalytic center, in particular chromium. The zinc compound is preferably used in the absence of visible and UV-radiation to increase its stability.

The zinc compound may be zinc metal; zinc-copper couple; activated zinc; an alkylzinc compound, in particular, dimethyl-, diethyl- or dibutylzinc; an arylzinc compound, such as diphenyl- or ditolylzinc; zinc amide, in particular, zinc pyrrolide or zinc-porphyrin complexes; zinc oxygenate (including formate, acetate, basic acetate, 2-ethylhexanoate, and other carboxylates of zinc); zinc halide, in particular anhydrous zinc chloride; or a combination thereof. It is preferable to use zinc compounds soluble in the solvents used in the oligomerization process.

The ratio of the components in the catalyst system, including the zinc compound, may vary. The aluminum: chromium molar ratio may be from 5:1 to 500:1, preferably from 10:1 to 100:1, most preferably from 20:1 to 50:1. The ligand:chromium molar ratio may vary from 2:1 to 50:1, preferably from 2.5:1 to 5:1. The zinc:chromium molar ratio may vary and ranges from 2:1 to 100:1, preferably from 5:1 to 50:1.

The catalyst system prepared by one of the above-disclosed method is fed to an oligomerization reactor by any method known in the art in diluted or undiluted form. It is preferable to dilute the catalyst system with a hydrocarbon solvent, for example, such as aliphatic or cycloaliphatic hydrocarbons comprising 6 to 16 carbon atoms, for example, undecane, cyclohexane, Isopar™ (ExxonMobil), or a mixture thereof. For the above reasons, it is especially preferable to dilute the catalyst system with saturated hydrocarbon solvents or a mixture thereof. However, it is preferable that the content of aromatic compounds does not exceed 2 wt. %.

The solvent in the oligomerization process may be a hydrocarbon solvent, for example, alkane, cycloalkane, or a mixture of various alkanes and/or cycloalkanes. The hydrocarbon solvent may also include unsaturated hydrocarbons, such as olefins or aromatic compounds. Suitable hydrocarbon solvents or components of the solvent include heptane, cyclohexane, decane, undecane, isodecane, and hexene-1.

The oligomerization process is carried out by contacting the catalyst system with raw material, which is olefins, such as ethylene (ethene), propylene (propene), and butylene (butene). The method for oligomerization of olefins is carried out to obtain higher olefins. Industrially important processes are the processes for preparing α-olefins from ethylene. α-Olefins are compounds with a carbon-carbon double bond (C=C) at the α-position. α-Olefins prepared in the oligomerization process may include various $C_5$-$C_{40}$ olefins and a mixture thereof. For example, α-olefins prepared in the process of oligomerization of ethylene may be pentene-1, hexene-1, heptene-1, octene-1, nonene-1, decene-1, undecene-1, dodecene-1, higher α-olefins, or a mixture thereof. The oligomerization process is preferably the process of trimerization of ethylene to produce hexene-1.

The oligomerization process may be carried out in any reactor known in the art. Suitable reactors include a stirred continuous reactor, a batch reactor, a plug flow reactor, and a tubular reactor. The reactor may be a gas-liquid reactor, for example, an autoclave with a stirrer, a bubble column (bubble reactor) with co- or counter gas/liquid flow, or a bubbling gas lift reactor.

The pressure of olefin-containing raw material in the oligomerization process is from 1 to 200 atm. In the preferred embodiment of the method, when the oligomerization process is trimerization of ethylene to produce hexene-1, the pressure of ethylene may vary from 1 to 200 atm, preferably from 10 to 60 atm, most preferably from 15 to 40 atm. It is preferred to increase the pressure of ethylene in order to increase the rate of oligomerization.

The temperature of the oligomerization process may range from 0 to 160° C., preferably from 40 to 130° C. It is most preferable to keep the temperature in the reactor between 80 and 120° C. At this temperature, a polymer by-product, in particular polyethylene, is not precipitated from the solution and is removed from the reactor in the form of a solution, and the catalyst system is most active and selective. The oligomerization process at higher temperature (above 120° C.) can lead to deactivation of the catalyst system.

In accordance with the claimed method, the reaction time may vary. The reaction time may be defined as the residence time of a raw material and a solvent in the oligomerization reaction zone. The reaction time for a continuous flow reactor can be defined as an average residence time. The reaction time may vary depending on the used olefin-containing raw material, reaction temperature, pressure and other process parameters. In embodiments of the method, the reaction time does not exceed 24 hours. The reaction time may be less than 12 h, less than 6 h, less than 3 h, less than 2 h, less than 1 h, less than 30 min, less than 15 min, and less than 10 min. The reaction time of from 30 min to 90 min is most preferred.

According to the claimed method, olefin and the catalyst system may enter into contact with hydrogen that is fed to the oligomerization reactor and is used as a diluent. Hydrogen can accelerate the oligomerization reaction and/or increase the activity of the organometallic catalyst. Further, hydrogen can reduce the amount of the formed polymer by-product and limit its deposition on the walls of the equipment.

The process of oligomerization of olefins is carried out in the absence of water and oxygen.

Raw material, a solvent, and the catalyst system may be fed to the oligomerization reactor in any order. It is preferable to add the components in the following order: a solvent, the catalyst system, followed by dosing starting olefins.

According to the claimed method, the effluent from the reactor may contain the organometallic catalyst, the target product, by-products, the solvent, and polymers that can be formed during the oligomerization process.

Olefin oligomers may include isomers of olefin, and the weight ratio of α-olefin to corresponding isomers must be at least 99.5:0.5.

The effluent from the reactor can be treated with an agent deactivating the catalyst system. Suitable deactivating agents known from the art include water, alcohols, amines, aminoalcohols, or a mixture thereof, and various sorbents, such as silica gel, aluminum oxide, alumosilicates or their mixture with water, alcohols, amines, or aminoalcohols. The alcohols include methanol, ethanol, n-propanol, iso-propanol, n-butanol, iso-butanol, tert-butanol, 2-ethylhexanol, ethylene glycol, propylene glycol, triethylene glycol, polyethylene glycol, or a mixture thereof. Examples of suitable amines include ammonia, methylamine, dimethylamine, trimethylamine, ethylamine, diethylamine, triethylamine, tri-n-propylamine, diisopropylethylamine, tri-n-butylamine, piperazine, pyridine, ethylenediamine, diethylenetriamine, or a mixture thereof. Examples of aminoalcohols include ethanolamine, diethanolamine, triethanolamine, methyldiethanolamine, dodecyl diethanolamine, 1-amino-2-propanol, or a mixture thereof. The preferred deactivating agent is an alcohol or aminoalcohol applied on silica gel.

The effluent from the reactor may be further cooled by passing it, for example, through a heat exchanger. The cooling of the effluent from the reactor may include mixing the hot effluent with the cooled effluent. The cooling of the effluent is carried out to a temperature of from 20° C. to 100° C., preferably to a temperature of less than 95° C., less than 90° C., less than 85° C., less than 80° C., less than 75° C., less than 70° C., less than 65° C., less than 60° C., less than 55° C., less than 50° C., less than 45° C., less than 40° C., less than 35° C., less than 30° C., and less than 25° C. The effluent may be cooled to ambient temperature, for example, to 20-25° C. The temperature to which the effluent is cooled is selected so as to increase the precipitation of polymer from the solvent.

Thus, the present invention provides an increased selectivity of the olefin oligomerization catalyst system to the yield of the target linear α-olefin compared to the yield of all its isomers, which, in turn, allows reducing the loss of the linear α-olefin during recycling thereof in the production of polyolefins. The isomeric purity of α-olefin, in particular hexene-1, reaches 99.9%.

The invention is further illustrated by the following examples.

Embodiments of the Invention

The reaction of oligomerization of ethylene is carried out using a catalyst system comprising: 1) a chromium source (chromium (III) 2-ethylhexanoate), 2) a nitrogen-containing ligand (2,5-dimethylpyrrole), 3) an alkylaluminum activator (triethylaluminum (TEA) and diethylaluminum chloride (DEAC), and 4) diethylzinc. The process of oligomerization of olefins, in particular trimerization of ethylene, is carried out under the action of this catalyst system to produce trimerization products.

Example 1. Preparation of a Catalyst System (Heating Alkylaluminum and Diethylzinc)

The ratio of the components of the prepared catalyst system: ligand:chromium:TEA:DEAC:zinc=3.2:1:32:16:16

2,5-Dimethylpyrrole (0.92 g, 9.7 mmol), ethylbenzene (73.4 g) and cyclohexane (21.5 g) are mixed in a 1000 mL glass flask. Chromium (III) 2-ethylhexanoate (2.32 g, 3.0 mmol) is added to the resulting mixture, mixed to homogenous consistency, and allowed to stand for 1 h at 20° C. under a nitrogen flow. A mixture of 25% solution of triethylaluminum in hexane (52 mL, 96.7 mmol), 15% solution of diethylaluminum chloride in hexane (54 mL, 47.8 mmol), and 1M solution of diethylzinc in hexane (47 mL, 47 mmol) is prepared in a separate vessel. The obtained mixture is heated to 62° C. and added to the first solution by portions of 20 mL for 20 min. The maximum temperature of the mixture is 37° C. (15 min after addition of the first solution), and then the temperature drops to 35° C. (over 45 min). The resulting solution becomes first brown and then dark yellow. A little grey (zinc) precipitate is observed. The resulting solution is used as a catalyst system for oligomerization of ethylene.

Example 2. Preparation of a Catalyst System (SHF Irradiation of Alkylaluminum and Diethylzinc)

The ratio of the components of the prepared catalyst system: ligand:chromium:TEA:DEAC:zinc=3.2:1:32:16:16

The process is carried out by the method described in Example 1, except that cyclohexane is not used and the mixture of solutions of triethylaluminum in hexane, diethylaluminum chloride in hexane, and diethylzinc in hexane is not heated but subjected to SHF irradiation (microwave irradiation) by portions of 50 mL in the chamber of a MARS-6 SHF irradiation (microwave irradiation) apparatus at a rated power of 400 W for 6 min at 25° C. Each subsequent portion of SHF-irradiated solutions of triethylaluminum, diethylaluminum chloride and diethylzinc is added to the solution of chromium (III) 2-ethylhexanoate and 2,5-dimethylpyrrole immediately after the irradiation for 30 sec. The resulting mixture is used as a catalyst system for oligomerization of ethylene.

Example 3. Preparation of a Catalyst System (Heating Alkylaluminum and Diethylzinc and Holding (Aging) the Catalyst System)

The ratio of the components of the prepared catalyst system: ligand:chromium:TEA:DEAC:zinc=3:1:31:13:15

2,5-Dimethylpyrrole (0.92 g, 9.7 mmol), ethylbenzene (69.3 g), and cyclohexane (15.6 g) are mixed in a 1000 mL glass flask. Chromium (III) 2-ethylhexanoate (2.43 g, 3.18 mmol) is added to the resulting mixture, mixed to homogenous consistency, and allowed to stand for 0.2 h at 20° C. under a nitrogen flow. A mixture of 25% solution of triethylaluminum in hexane (53 mL, 98.6 mmol), 15% solution of diethylaluminum chloride in hexane (48 mL, 42.5 mmol), and 1M solution of diethylzinc in hexane (48 mL, 48 mmol) is prepared in a separate vessel. The resulting mixture is heated to 62° C. (the mixture becomes grey, and a small amount of zinc is precipitated) and is added to the first solution by portions of 20 mL for 20 min. The maximum temperature of the mixture is 37° C. (15 min after addition of the first solution), and then the temperature drops to 35° C. (over 45 min). The resulting solution becomes first brown and then dirty green (mousse). A little grey (zinc) precipitate is observed. The resulting solution is hold (aged) under nitrogen for a period of time as indicated in Table 1 and then is used as a catalyst system for oligomerization of ethylene.

Example 4. Preparation of a Catalyst System (Heating and SHF Irradiation of Alkylaluminum and Diethylzinc)

Method 1

The ratio of the components of the prepared catalyst system: ligand:chromium:TEA:DEAC:zinc=3:1:30:15:15

2,5-Dimethylpyrrole (0,275 g, 2.9 mmol) and ethylbenzene (21.7 g) are mixed in a 1000 mL glass flask, and chromium (III) 2-ethylhexanoate (0.463 g, 0.96 mmol) is added thereto, mixed to homogenous consistency and allowed to stand for 0.2 h at 20° C. under a nitrogen flow. A mixture of 25% solution of triethylaluminum in hexane (15.5 mL, 28.9 mmol), 15% solution of diethylaluminum chloride in hexane (16.3 mL, 14.4 mmol), and 1M solution of diethylzinc in hexane (14.2 mL, 14.2 mmol) is prepared in a separate vessel to obtain solution 2 that is heated to 66° C. under a nitrogen flow at reflux (the mixture becomes grey, and a small amount of zinc is precipitated), and first 50 mL of the mixture are subjected to SHF irradiation in the chamber of a MARS-6 SHF irradiation apparatus at a rated power of 400 W for 6 min. Then, this portion is quickly added to solution 1 to obtain solution 3. Then subsequent 50 mL of the mixture of organometallic compounds are irradiated for 60 sec. This portion is quickly added to obtained solution 3. Then subsequent 50 mL of the mixture of organometallic compounds are irradiated for 90 sec. This portion is quickly added to solution 3. The resulting solution becomes first brown and then dirty green (mousse). A little grey (zinc) precipitate is observed. The resulting solution is used as a catalyst system for oligomerization of ethylene.

Example 5. Preparation of a Catalyst System (Heating and SHF Irradiation of Alkylaluminum)

Method 2

The ratio of the components of the prepared catalyst system: ligand:chromium:TEA:DEAC:zinc=3:1:30:15:15

2,5-Dimethylpyrrole (2.20 g, 23.1 mmol) and ethylbenzene (173.3 g) are mixed in a 1000 mL glass flask, and chromium (III) 2-ethylhexanoate (3.70 g, 7.69 mmol) is added thereto, mixed to homogenous consistency, and then the solvent is degased and a nitrogen atmosphere is created in the vessel by repeated degassing to 40 mbar/adding nitrogen (3-4 times) (to obtain solution 1). A mixture of 25% solution of triethylaluminum in hexane (124 mL, 230.8 mmol) and 15% solution of diethylaluminum chloride in hexane (130.4 mL, 115.4 mmol) is prepared in a separate vessel to obtain solution 2. The catalyst solution (0.5 mL) prepared in Example 2 is added to solution 2 to obtain solution 3. Then, 125 mL of solution 3 is subjected to SHF irradiation in the chamber of a MARS-6 SHF irradiation apparatus at a rated power of 200 W for 60 sec. Solution 3 starts to boiling. Hot solution 3 is quickly added to solution 1 along the wall of the flask. The mixture is allowed to stand at room temperature without stirring. After 20 min, the residual solution 3 at 20° C. and 1M solution of diethylzinc in hexane (113.4 mL, 113.4 mmol) are added to the obtained mixture. The resulting solution is used as a catalyst system for oligomerization of ethylene.

Example 6. Preparation of a Catalyst System in the Absence of Visible and UV-Radiation The process is carried out by the method described in Example 3, except that the chromium source is a salt prepared by the method disclosed in application WO2011093748 (p. 15), wherein the content of chromium is 14.75%, as determined by the ICP-MS method. In addition, the used flask is made of dark glass preventing the penetration of visible and UV-radiation. Upon sampling, grey precipitate (zinc) from the catalyst system is not observed.

Example 7. Oligomerization of Ethylene in a Stirred Reactor

A catalyst system was prepared by the methods described in Examples 1-4. Then the prepared catalyst system is aged under nitrogen for several days (see Table 1) and is used in the process of oligomerization of ethylene in a batch mode.

A required amount (Table 1) of a solution of the catalyst system is added to dried cyclohexane (150 mL) under nitrogen, then the obtained mixture is transferred due to pressure differences, to an evacuated 300 ml Parr reactor. Hydrogen (2 atm) is dosed to the reactor, and thermal conditioning of the contents under stirring (650 rpm) is provided by circulation of the coolant having a temperature of 103° C., inside the jacket of the reactor until the temperature stabilizes within a range of 97 to 99° C. Then ethylene is continuously dosed to the reactor to a total pressure of X+3 atm, wherein X is a desired partial pressure of ethylene (Table 1), and the dosing is continued at a constant pressure as the gas is consumed (the temperature inside the reactor is between 100 and 110° C.) After 30 or 60 min, the dosing of ethylene is terminated, the mixture is cooled to from 55 to 60° C., and the liquid phase is drained, while degassing ethylene, through a lower ball valve. Then, silica gel (5 g) is added to the liquid phase, the mixture is cooled, and analyzed by gas chromatography (GC).

The purity of hexene-1 is estimated by the ratio of peaks of hexene-1, cis-hexene-2, and trans-hexene-2. The test results are given in Table 1.

Example 8. Oligomerization of Ethylene in a Bubble Column Reactor

The catalyst system is prepared by the method described in Example 4. A solution of the catalyst system diluted with cyclohexane to a concentration of 5 mg/kg is fed at a rate of 2 kg/h into the annular space of a bubble column reactor with a thermostatic jacket. The flow rate of ethylene is 300 g/h, and the flow rate of hydrogen is 0.16 g/h. The process is carried out for 72 hours at an average pressure of 15 atm and an average temperature of 102° C. The average concentration of hexene-1 at the outlet of the reactor is 7.7% over 72 h. The purity of hexene-1 is 99.65% (not adjusted for the accumulation of isomeric hexenes in the recycled solvent).

TABLE 1

Results of the process of oligomerization of ethylene in cyclohexane with different catalysts at different pressures and concentrations of chromium

| No | Catalyst in example No. | SHF | T | t, h | P, atm | M(Cr), mg | Days* | C(C6-1), % | S(C6-1), % | Y, g | A, kg/g*h | S, % |
|---|---|---|---|---|---|---|---|---|---|---|---|---|
| 1 | 2 | + | − |   |   | 3.33 | 0 | 23.5 | 99.1 | 44 | 13 | 89.4 |
| 2 |   |   |   | 1 | 15 | 0.66 |   | 21.1 | 99.5 | 36 | 54 | 92.9 |
| 3 |   |   |   |   |   |   |   | 18.0 | 99.4 | 29 | 44 | 93.3 |
| 4 | 2 | + | − |   |   | 2 | 1 | 21.0 | 99.4 | 36 | 36 | 92.8 |
| 5 |   |   |   | 0.5 | 20 | 0.66 |   | 21.2 | 99.6 | 35 | 106 | 94.0 |
| 6 |   |   |   |   |   |   |   | 17.1 | 99.5 | 26 | 79 | 94.9 |
| 7 | 1 | − | + | 0.5 | 20 | 3 | 50 | 19.5 | 98.7 | 36 | 24 | 88.4 |
| 8 |   |   |   |   |   |   |   | 17.2 | 97.2 | 31 | 21 | 86.5 |
| 9 |   |   |   |   |   |   |   | 23.6 | 99.8 | 46 | 31 | 89.0 |
| 10 |   |   |   |   |   | 1.8 | 21 | 26.4 | 99.0 | 51 | 56 | 89.7 |
| 11 |   |   |   |   |   | 1.2 | 50 | 19.1 | 99.9 | 32 | 53 | 93.7 |
| 12 |   |   |   |   |   |   |   | 28.8 | 99.9 | 59 | 98 | 90.0 |
| 13 |   |   |   |   |   | 0.6 | 21 | 16.1 | 99.6 | 25 | 83 | 95.0 |
| 14 |   |   |   |   |   |   | 22 | 12.2 | 99.5 | 18 | 60 | 96.0 |
| 15 |   |   |   |   |   |   |   | 13.8 | 99.3 | 20 | 66 | 95.3 |
| 16 | 1 | − | + | 0.5 | 24 | 0.6 |   | 16.7 | 99.5 | 25 | 83 | 95.4 |
| 17 | 1 | − | + | 0.5 | 30 | 3.6 | 28 | 16.7 | 97.4 | 30 | 17 | 87.4 |
| 18 |   |   |   |   |   | 0.6 |   | 21.9 | 99.6 | 37 | 122 | 93.7 |
| 19 |   |   |   |   |   |   |   | 27.8 | 99.6 | 52 | 172 | 93.0 |
| 20 | 3 | − | + | 0.5 | 15 | 3 | 2 | 14.4 | 98.3 | 24 | 15 | 89.4 |
| 21 |   |   |   |   |   | 0.6 |   | 14.5 | 99.6 | 22 | 74 | 93.8 |
| 22 |   |   |   |   |   |   |   | 14.7 | 99.7 | 23 | 77 | 93.8 |
| 23 | 3 | − | + | 0.5 | 20 | 3 | 3 | 24.9 | 99.2 | 48 | 32 | 89.5 |
| 24 |   |   |   |   |   |   |   | 27.7 | 99.3 | 57 | 37 | 88.7 |
| 25 |   |   |   |   |   | 1.2 | 18 | 25.3 | 99.9 | 49 | 81 | 89.9 |
| 26 |   |   |   |   |   |   |   | 20.8 | 99.9 | 36 | 60 | 93.0 |
| 27 |   |   |   |   |   | 0.6 | 3 | 14.0 | 99.6 | 21 | 70 | 93.6 |
| 28 |   |   |   |   |   |   |   | 16.0 | 99.5 | 25 | 84 | 94.1 |
| 29 | 3 | − | + | 0.5 | 25 | 3 | 10 | 32.5 | 99.2 | 76 | 51 | 86.1 |
| 30 |   |   |   |   |   |   |   | 30.1 | 99.2 | 66 | 44 | 87.3 |
| 31 | 4 | + | + | 0.5 | 20 | 3.33 | 2 | 25.5 | 99.9 | 48 | 29 | 91.6 |
| 32 |   |   |   |   |   |   |   | 29.2 | 99.2 | 62 | 37 | 88.7 |
| 33 |   |   |   |   |   | 1.33 |   | 17.2 | 99.9 | 27 | 41 | 94.2 |
| 34 |   |   |   |   |   |   | 10 | 11.4 | 99.9 | 17 | 26 | 94.4 |
| 35 |   |   |   |   |   |   |   | 22.2 | 99.9 | 40 | 60 | 92.0 |
| 36 |   |   |   |   |   | 0.66 | 0 | 15.3 | 99.9 | 24 | 73 | 95.0 |
| 37 |   |   |   |   |   |   |   | 13.3 | 99.9 | 20 | 61 | 95.0 |

TABLE 1-continued

Results of the process of oligomerization of ethylene in cyclohexane with
different catalysts at different pressures and concentrations of chromium

| No | Catalyst in example No. | SHF | T | t, h | P, atm | M(Cr), mg | Days* | C(C6-1), % | S(C6-1), % | Y, g | A, kg/g*h | S, % |
|---|---|---|---|---|---|---|---|---|---|---|---|---|
| 38 | 4 | + | + | 0.5 | 15 | 3.33 | 6 | 17.2 | 98.3 | 30 | 18 | 88.6 |
| 39 | | | | | | | | 15.1 | 98.1 | 25 | 15 | 89.6 |
| 40 | | | | | | 1.33 | | 14.8 | 99.9 | 23 | 35 | 93.5 | t—duration of the oligomerization process
T—heating
"+"—heating is used;
"−"—heating is absent
*—time of aging the catalyst system
C(C6-1)—concentration of hexene-1 in a solution, as defined by gas chromatography
S(C6-1)—selectivity to hexene-1 among isomers
Y—yield of olefins
A—activity of the catalyst system (1 kg of olefins per 1 g of chromium per hour);
S—ratio of the hexene-1 concentration to the sum of concentrations of hexene-1 and all decenes.

The results of experiments 2, 3, 5, and 6 and data in Table 1 show that the selectivity to hexene-1 (compared to all isomers) of the catalyst system with an activator and diethylzinc, which are SHF-irradiated, is 99.4-99.6% with an average activity of 93 kg/g*h at 20 atm and a weight of chromium of 0.66 mg. In addition, the catalyst system in which organometallic components were pre-heated has selectivity to hexene-1 of, for example, 99.5-99.6% (experiments 27, 28) with an average activity of about 77 kg/g*h at 20 atm and a weight of chromium of 0.6 mg.

The results of experiments 36 and 37 show that the selectivity of the catalyst system to hexene-1 increases to 99.9% when alkylaluminum and diethylzinc are subjected to both heating and SHF irradiation during the preparation of the catalyst system. The average activity of the catalyst system is 67 kg/g*h at 20 atm, and a weight of chromium is 0.66 mg.

The results of experiments 11, 12, 25, and 26 show that pre-heating of some of the components of the catalyst system, followed by holding (aging) the catalyst system for 18-50 days at room temperature results in an increase in the selectivity to hexene-1 to 99.9%. In this case, there is no need for SHF irradiation. The average activity of the catalyst system is 70 to 76 kg/g*h at 20 atm, and a weight of chromium is 1.2 mg.

The present invention provides an increased selectivity of the olefin oligomerization catalyst system to the yield of the target linear α-olefin compared to the yield of all its isomers, which, in turn, allows reducing the loss of the linear α-olefin during recycling thereof in the production of polyolefins. The isomeric purity of α-olefin, in particular hexene-1, reaches 99.9%.

The invention claimed is:

1. A method for preparing a catalyst system used in a process of oligomerization of olefins to produce at least 99.9% isomeric purity of hexene-1, which is characterized by comprising mixing a chromium source compound, a nitrogen-containing ligand, alkylaluminum, and a zinc compound, characterized in that the alkylaluminum or a mixture of the alkylaluminum and the zinc compound is activated by heating and SHF irradiation (microwave irradiation) prior to the mixing thereof with the other components of the catalyst system, wherein the heating of the alkylaluminum or the mixture of the alkylaluminum and the zinc compound during the preparation of the catalyst system is carried out up to 66 C.

2. The method of claim 1 characterized in that the chromium source compound is a compound of the general formula $CrX_n$, wherein X are the same or different organic or non-organic substituents, and n is an integer of from 1 to 6.

3. The method of claim 2 characterized in that X are organic substituents comprising 1 to 20 carbon atoms, selected from the group including alkyl, alkoxy, carboxyl, acetylacetonate, amino, and amido; or non-organic substituents selected from the group including halides, sulfates, and chromium oxides.

4. The method of any one of claims 1 to 3 characterized in that the chromium source compound is a compound selected from the group including chromium (III) chloride, chromium (III) acetate, chromium (III) 2-ethylhexanoate, chromium (III) acetylacetonate, chromium (III) pyrrolide, chromium (II) acetate, and chromium (IV) dioxide dichloride ($CrO_2Cl_2$).

5. The method of claim 1 characterized in that the nitrogen-containing ligand is a pyrrole ring-containing organic compound.

6. The method of claim 1 characterized in that the nitrogen-containing ligand is a compound selected from the group including pyrrole, 2,5-dimethylpyrrole, lithium pyrrolide ($C_4H_4NLi$), 2-ethylpyrrole, indole, 2-methylindole, and 4,5,6,7-tetrahydroindole.

7. The method of claim 1 characterized in that the alkylaluminum is a compound selected from the group including triethylaluminum, diethylaluminum chloride, tripropylaluminum, triisobutylaluminum, diethylaluminum ethoxide, ethylaluminum sesquichloride, or a mixture thereof.

8. The method of claim 1 characterized in that the zinc compound is a compound selected from the group including zinc metal, zinc-copper couple, activated zinc, alkylzinc compounds, arylzinc compounds, zinc amides, zinc oxygenates, and zinc halides or a combination thereof.

9. The method of claim 8 characterized in that, the alkylzinc is a compound selected from the group including dimethyl-, diethyl- and dibutylzinc.

10. The method of claim 8 characterized in that, the arylzinc is a compound selected from the group including diphenyl- and ditolylzinc.

11. The method of claim 8 characterized in that, the zinc oxygenate is a compound selected from the group including formate, acetate, acetate and 2-ethylhexanoate.

12. The method of claim 8 characterized in that, the zinc halide is an anhydrous zinc chloride.

13. The method of claim 1 characterized in that, during the preparation of the catalyst system, the zinc compound is used in the absence of visible and UV-radiation.

14. The method of claim 1, characterized in that a molar ratio of aluminum/chromium in the catalyst system is from 5:1 to 500:1.

15. The method of claim 14, characterized in that a molar ratio of aluminum/chromium in the catalyst system is from 10:1 to 100:1.

16. The method of claim 15, characterized in that a molar ratio of aluminum/chromium in the catalyst system is from 20:1 to 50:1.

17. The method of claim 1, characterized in that a molar ratio of ligand/chromium in the catalyst system is from 2:1 to 50:1.

18. The method of claim 17, characterized in that a molar ratio of ligand/chromium in the catalyst system is from 2.5:1 to 5:1.

19. The method of claim 1, characterized in that a molar ratio of zinc/chromium in the catalyst system is from 2:1 to 100:1.

20. The method of claim 19, characterized in that a molar ratio of zinc/chromium in the catalyst system is from 5:1 to 50:1.

21. The method of claim 1, characterized in that the heating of the alkylaluminum or the mixture of the alkylaluminum and the zinc compound during the preparation of the catalyst system is carried out at least 40° C. and up to 66° C.

22. The method of claim 21, characterized in that the heating of the alkylaluminum or the mixture of the alkylaluminum and the zinc compound during the preparation of the catalyst system is carried out at least 50° C. and up to 66° C.

23. The method of claim 22, characterized in that the heating of the alkylaluminum or the mixture of the alkylaluminum and the zinc compound during the preparation of the catalyst system is carried out at least 60° C. and up to 66° C.

24. The method of claim 1, characterized in that the frequency of the SHF radiation (microwave radiation) is selected between 0.2 and 20 GHz.

25. The method of claim 24, characterized in that the frequency of the SHF radiation (microwave radiation) is 2.45 GHz.

26. The method of claim 24, characterized in that the time of the SHF irradiation (microwave irradiation) is from 20 seconds to 20 minutes.

27. The method of claim 1, characterized in that the mixing of the alkylaluminum or the mixture of the alkylaluminum and the zinc compound, which are activated by heating or SHF irradiation, with the chromium source and the nitrogen-containing ligand is carried out not more than 3 minutes after the irradiation.

28. The method of claim 27, characterized in that the mixing of the alkylaluminum or the mixture of the alkylaluminum and the zinc compound, which are activated by heating or SHF irradiation, with the chromium source and the nitrogen-containing ligand is carried out not more than 1 minutes after the irradiation.

* * * * *